(12) United States Patent
Durban et al.

(10) Patent No.: US 12,061,332 B2
(45) Date of Patent: Aug. 13, 2024

(54) METHOD AND DEVICE FOR PROJECTING A PATTERN OF INTEREST ON A MODIFIED RETINAL AREA OF A HUMAN EYE

(71) Applicant: PIXIUM VISION SA, Paris (FR)

(72) Inventors: Bastien Durban, Paris (FR); Jean-Baptiste Floderer, Paris (FR); Maxime Denefle, Sucy en Brie (FR); Martin Deterre, Paris (FR)

(73) Assignee: PIXIUM VISION SA, Paris (FR)

( * ) Notice: Subject to any disclaimer, the term of this patent is extended or adjusted under 35 U.S.C. 154(b) by 265 days.

(21) Appl. No.: 17/593,275

(22) PCT Filed: Mar. 27, 2020

(86) PCT No.: PCT/EP2020/058875
§ 371 (c)(1),
(2) Date: Sep. 14, 2021

(87) PCT Pub. No.: WO2020/193798
PCT Pub. Date: Oct. 1, 2020

(65) Prior Publication Data
US 2022/0201258 A1 Jun. 23, 2022

(30) Foreign Application Priority Data
Mar. 28, 2019 (WO) .................. PCT/EP2019/057967

(51) Int. Cl.
*A61N 1/05* (2006.01)
*G02B 26/08* (2006.01)
*H04N 9/31* (2006.01)

(52) U.S. Cl.
CPC ....... *G02B 26/0833* (2013.01); *H04N 9/3179* (2013.01); *A61N 1/0543* (2013.01)

(58) Field of Classification Search
CPC .............. G02B 26/0833; H04N 9/3179; A61N 1/0543; A61B 3/0008
USPC .................................................. 382/183, 182
See application file for complete search history.

(56) References Cited

U.S. PATENT DOCUMENTS

| | | | |
|---|---|---|---|
| 8,956,396 B1 * | 2/2015 | Friend .................. | A61N 5/0622 607/88 |
| 2003/0181957 A1 * | 9/2003 | Greenberg ......... | A61N 1/36046 607/54 |
| 2007/0055336 A1 * | 3/2007 | Greenberg ......... | A61N 1/37223 607/54 |
| 2009/0312818 A1 * | 12/2009 | Horsager ............. | A61N 1/0543 607/54 |
| 2015/0234187 A1 * | 8/2015 | Lee ...................... | G02B 26/005 345/8 |

(Continued)

*Primary Examiner* — Ali Bayat
(74) *Attorney, Agent, or Firm* — Workman Nydegger (57) ABSTRACT

The present invention pertains to a method for projecting a pattern of interest on a modified retinal area of a human eye, comprising the steps of providing a pulsed input light beam, modulation and dividing the pulsed input light beam into a pulsed modulated light pattern of modulated pulsed sub-beams based on a pattern of interest, wherein the modulated light pattern forms a pulsed output beam reflecting the pattern of interest, wherein performing an individual pulse width modulation of a modulation duty cycle of the modulated individual sub-beams forming the output beam, and to correspondingly adapted device.

19 Claims, 5 Drawing Sheets

(56) References Cited

U.S. PATENT DOCUMENTS

2017/0316487 A1* 11/2017 Mazed .............. G06Q 30/0241

* cited by examiner

METHOD AND DEVICE FOR PROJECTING A PATTERN OF INTEREST ON A MODIFIED RETINAL AREA OF A HUMAN EYE

CROSS-REFERENCE TO RELATED APPLICATIONS

The present application is a 371 US National Stage Entry of PCT International Application No. PCT/EP2020/058875, filed Mar. 27, 2020, which claims priority to PCT International Application No. PCT/EP2019/057967, filed Mar. 28, 2019, the entire contents of which are incorporated by reference herein.

TECHNICAL FIELD

The invention relates to a method for projecting a pattern of interest on an area of a human retina that has been modified to restore its photosensitive characteristics, for instance via implantation of a retinal implant, and a corresponding device.

TECHNOLOGICAL BACKGROUND

Retinal malfunction, particular caused by degenerative retinal diseases, is a leading reason for visual impairment or even blindness.

For at least partially restoring a patient's visual function, it is known to make use of modifications of a retinal area of the human eye, for instance by making use of a retinal implant or in other words retinal prosthesis. In this regard, several different types of retinal implants are known, which are based on different working principles.

Retinal implants have in common that they are usually placed subretinally, epiretinally, or suprachoroidally in the eye of the patient, such that they can replace in effect the damaged photoreceptors. In this regard, information about a visual scene is captured with a camera and then transmitted to an electrode array implanted in the retina.

Among common retinal implants, implants are known which comprise skin-penetrating wires. These wires introduce risks of infection and scarring. Thus, more modern implants use different wireless techniques, for instance by delivering power and visual information through inductive coils. Furthermore, it is known to deliver power inductively and visual information optically through the pupil of the eye, or to deliver both visual information and power optically.

A particularly beneficial type of wireless information transfer retinal implants is based on projecting stimulation patterns of preferably infrared light into the eye. When the gaze direction is such that some part of the implants is illuminated by part of the pattern, the implant converts that part of the signal to electrical current that stimulates the retina accordingly.

The retinal implant is an array composed of stimulation electrodes or pixels. Each pixel has one or several photodiodes that capture the light delivered from a visual processor and converts it into electrical current for stimulation.

Several implant arrays can be placed in the subretinal space, typically in or close to the foveal area.

Alternatively, an approach, known as optogenetics, has been proposed to treat the residual retinal cells to restore their photosensitive behavior by gene therapy. Optogenetics refers to the combination of genetics and optics to control well-defined events within specific cells of living tissue. Optogenetics consists in (i) genetically modifying target cells in order to render them sensitive to light by the expression of exogenous photoreactive proteins in cellular membrane and (ii) providing illuminating device able to provide light to said photoreactive proteins.

In the following paragraphs of this patent, such a retinal area of the human eye that has been modified to restore photosensitive behavior through implantation of a retinal prosthesis or modification by optogenetics will be referred to as "modified retinal area".

For projecting light or a light beam, respectively, into a human eye, it is known to use a projector device, such as augmented reality goggles. A projector unit, for example projector optics, of the projector device projects a pulsed light beam onto and at least partially into the human eye. That is, the picture to be transmitted is transferred into the eye through its eye pupil and towards the retina.

Although it thereby is possible to provide the patient with an illuminated pattern of interest, the patient is merely able to sense a single light/dark contrast, as the irradiation is constant for each pulse of the pulsed light beam.

Nevertheless, safety issues are associated with the use of such projector device. For example, it is necessary that the projector device and method of use ensure that the irradiation on the retina is respecting a specific duty cycle, for instance smaller than 0.5, may be requested to ensure proper safety of the modified retinal area, for instance of a retina implant, for instance to ensure implant pulsed electrical function and proper electrical discharges between electrical pulses.

Similarly, it is necessary that the projector device and method of use ensure that the irradiation on the retina is respecting a duty cycle may also be required for optical safety to ensure that the average optical irradiance does not reach safety threshold. That way a high optical irradiance can be acceptable if modulated with a low enough duty cycle. This can be done by providing commands to the light source to shut down regularly between pulses at a specific duty cycle. It can also be done by ensuring that the micromirrors are OFF down regularly between pulses at a specific duty cycle. However, for medical application, it is typically required that safety, and related duty cycle, shall be ensured even in single fault condition.

SUMMARY OF THE INVENTION

It is an object of the present invention to provide an improved method for projecting a pattern of interest on a modified retinal area of a human eye, and a corresponding device for projecting a pattern of interest on this modified retinal area.

The above object is solved by means of a method for projecting a pattern of interest on a modified retinal area of a human eye comprising the features of claim 1. Further preferred embodiments are presented in the dependent claims, the description and the figures.

Accordingly, in a first aspect, a method for projecting a pattern of interest on a modified retinal area of a human eye or a method of operating a device as described herein for projecting a pattern of interest is suggested, which comprises the steps of providing a pulsed input light beam, preferably comprising coherent light or incoherent light and/or preferably light having a wavelength in the near infrared field, and modulating and dividing the pulsed input light beam into a pulsed and modulated light pattern of modulated pulsed sub-beams based on the pattern of interest, wherein the modulated light pattern forms a pulsed output beam reflecting the pattern of interest. The method is characterized by the step of performing an individual pulse width modulation of a modulation duty cycle of the modulated individual sub-beams forming the output beam.

By the individual pulse width modulation of the individual sub-beams, an irradiation duration of each sub-beam can individually be controlled, as the modulation duty cycle of each sub-beam can be individually and separately adjusted. That is, for each period of the pulsed output beam, the irradiation duration at a retinal implant the output beam is directed to can be varied within the output beam, as each sub-beam may comprise an individual duty cycle. Hence, the photodiodes of the retinal implant may be exposed to different irradiation durations which in turn lead to different stimulation currents and/or different durations of stimulation of the retina. Thereby, a grey level perception on the projected pattern irradiated via the output beam may be achieved. With other words, thus, it may be possible to illuminate the retina with patterns that are converted into different perceived grey levels within one pulse period. Hence, a patient provided with an according photosensitive retinal implant may be able to sense or perceive at least a rudimentary grayscale image. The latter may improve or facilitate orientation of the patient and may increase the visual faculty.

A pattern of interest here may be based on a picture or image which is captured and which is to be projected, wherein the picture or image may comprise dark and bright zones, preferably pixels, comprising different brightness values.

Preferably, the modified retinal area may be provided via implantation of a retinal prosthesis.

According to a further exemplary embodiment, the input light beam comprises a constant peak irradiance. Thereby, the irradiance hitting the retinal implant may be precisely identified, determined and/or calculated. Hence, both reliable operation of the retinal implant and prevention of damages at the retina due to an unknown excessive irradiance may be achieved.

Alternatively or in addition, the input light beam may comprise substantially the form of a pulse wave, as a such formed light beam may bear the advantage of a substantially constant irradiation during each duty cycle.

Preferably, the input light beam comprises a constant period.

According to another preferred embodiment, the input light beam comprises a constant duty cycle. Alternatively, the duty cycle of the input light beam is controlled.

Optimal adaption of a grayscale distribution inside the output beam may be achieved when, according to yet another preferred embodiment, a modulation period is synchronized with the period of the pulsed input light beam. With other words, a period of the pulse width modulation and hence of the sub-beams, which correspond to the modulation period, is synchronized with the period of the pulsed input light beam.

The method may be optimized in that, according to another preferred embodiment, a maximum individual modulation duty cycle of the individual sub-beams corresponds to the duty cycle of the pulsed input light beam.

To prevent damages at the retina due to an excessive irradiation, the duty cycle of the pulsed input light beam may preferably be equal to or smaller than 0.5, preferably 0.4, particularly preferably 0.3 of the period of the pulsed input light beam, and/or a maximum possible duty cycle of the sub-beams may preferably be equal to or smaller than 0.5, preferably 0.4, particularly preferably 0.3 of the period of the pulsed input light beam.

According to another preferred embodiment, the pattern of interest is obtained by capturing visual information, preferably an image, and dividing the captured visual information, preferably the captured image, into a pattern of pixels forming the pattern of interest, wherein the pixels at least reflect different brightness values if present within the visual information, preferably within the image.

Preferably an optional image processing of the captured image is performed prior to allocating the brightness values to pixels or regions of the processed image.

The above object is furthermore solved by means of a device for projecting a pattern of interest on a modified retinal area preferably comprising a retinal implant, of a human eye comprising the features of claim 7. Further preferred embodiments are presented in the dependent claims, the description, and the figures.

Accordingly, in a second aspect, a device for projecting a pattern of interest on a modified retinal area of a human eye is suggested, comprising a light source for providing a pulsed input light beam, preferably a light beam of preferably coherent light or incoherent light, preferably light having a wavelength in the near infrared field, and a modulation micromirror array for modulating and dividing the pulsed input light beam into a modulated light pattern of modulated pulsed sub-beams, wherein an orientation of each of the micromirrors of the micromirror array is individually controllable based on the pattern of interest, such that the sub-beams form a pulsed output beam reflecting the pattern of interest. The device further is formed and adapted to perform an individual pulse width modulation of the sub-beams forming the output beam by individually controlling a modulated duty cycle of the individual micromirrors.

By means of the device, the effects and advantages described with respect to the method above may be achieved.

According to a preferred embodiment, the device is further adapted such that a modulation period of the orientation control of the micromirrors is synchronized with the period of the pulsed input light beam.

For synchronization of the modulation by means of the micromirror array and the input light beam pulsing, a maximum individual modulation duty cycle of the micromirrors may preferably correspond to the duty cycle of the pulsed input light beam.

For prevention of damages at the retina caused by the output light beam, the duty cycle of the pulsed input light beam may preferably be set equal to or smaller than 0.5, preferably 0.4, particularly preferably 0.3 to the period of the pulsed input light beam, and/or a maximum possible modulation duty cycle of the sub-beams may preferably be equal to or smaller than 0.5, preferably 0.4, particularly preferably 0.3 to the period of the pulsed input light beam.

According to another preferred embodiment, the device may further comprise a camera for capturing visual information, preferably an image, and/or a processing unit for dividing the captured visual information, preferably the captured image, into a pattern of pixels forming the pattern of interest, wherein the pixels at least reflect different brightness values if present within the visual information, preferably within the image.

Moreover, it is important to note that for wearable electronics such as projector device, battery life has to be as high as possible to ensure maximum runtime between battery or power charge. Therefore, for a given reasonable battery size, the electrical power consumption of the device has to be minimized. Advantageously, the light source modulation proposed according to the present invention permits to have the source shutting down regularly between pulsed, hence significantly lowering its power consumption. Moreover, the fact that it is operating only a fraction of time limits the power consumption needed to cool the laser source, via a Peltier element or a fan operation for instance. Therefore, pulsing the laser source at a specific duty cycle significantly enhances battery lifetime.

BRIEF DESCRIPTION OF THE DRAWINGS

The present disclosure will be more readily appreciated by reference to the following detailed description when being considered in connection with the accompanying drawings in which.

DETAILED DESCRIPTION OF PREFERRED EMBODIMENTS

In the following, the invention will be explained in more detail with reference to the accompanying figures. In the Figures, like elements are denoted by identical reference numerals and repeated description thereof may be omitted in order to avoid redundancies.

Figure 1:
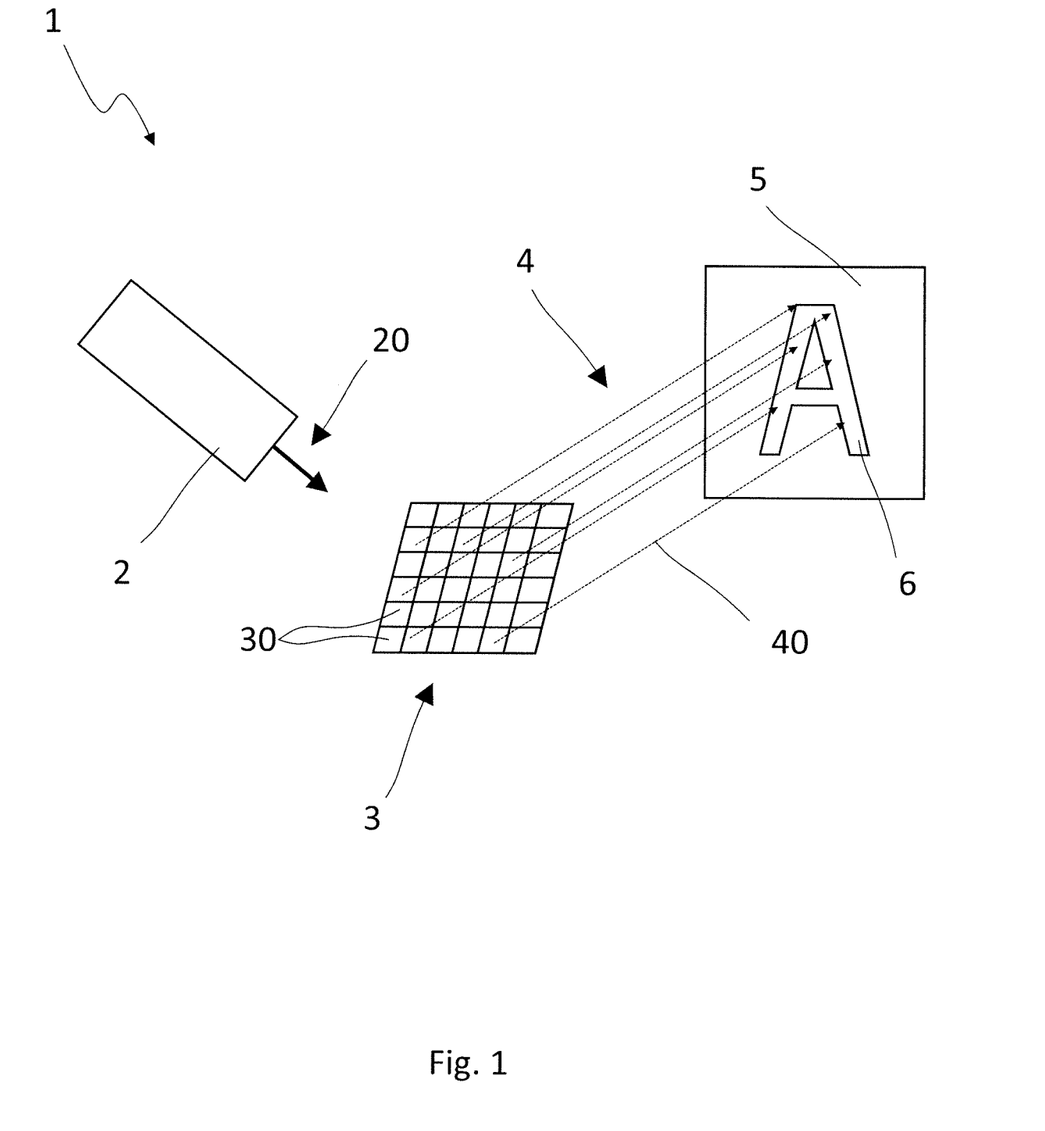
FIG. 1 schematically shows a device for projecting a pattern of interest on a photosensitive modified retinal area of a human eye.

FIG. 1 schematically shows a device 1 for projecting a pattern of interest 6 on a modified retinal area 5 of a human eye. The device 1 comprises a light source 2 which provides a pulsed input light beam 20 comprising light having a wavelength in the near infrared field.

The input light beam 20 is directed onto a modulation micromirror array 3 comprising a plurality of micromirrors 30 which can individually be operated such that an orientation of each of the micromirrors 30 can individually be adjusted and/or controlled. The modulation micromirror array 3 according to this specific embodiment is provided in form of a per se known digital micromirror device.

By means of the micromirror array 3, the input light beam 20 is reflected thereby forming an output beam 4. The output beam 4 consists of a plurality of sub-beams 40, into which the input beam 20 is divided when hitting on the individual micromirrors 30 of the micromirror array 3. The orientation of the micromirrors 30 is individually adjusted, such that a pattern of interest 6 which is to be projected onto a modified retinal area 5 are reflected by the plurality of sub-beams 40.

In this regard, the pattern of interest 6 is based on an image captured by a camera (not shown) which has been processed into a digital pattern of pixels, wherein the pixels comprise a grayscale value corresponding to a brightness value of the respective region of the image. Such data processing is per se known.

That is, only those micromirrors 30 which corresponds to a pixel comprising a brightness value above a predetermined threshold value are controlled to reflect the input light beam 20, wherein micromirrors 30 corresponding to pixels comprising a brightness value below the predetermined threshold value are oriented such that they do not contribute to forming the output beam 4.

Optionally, the modified retinal area 5 may comprise a retinal implant, preferably a photosensitive retinal implant.

Hence, the output beam 4 substantially reflects the pattern of interest 6. When the output beam 4 hits the modified retinal area 5, only those parts of the modified retinal area 5 comprising the retinal implant are illuminated by means of the output beam 4 or in particular the sub-beams 40, which reflect the pattern of interest at the retinal implant. Consequently, only those photosensitive diodes of the retinal implant convert light into electric current, which are arranged in the projected pattern of interest 6. A person comprising the retinal implant, thus, can perceive the pattern of interest 6.

Figure 2:
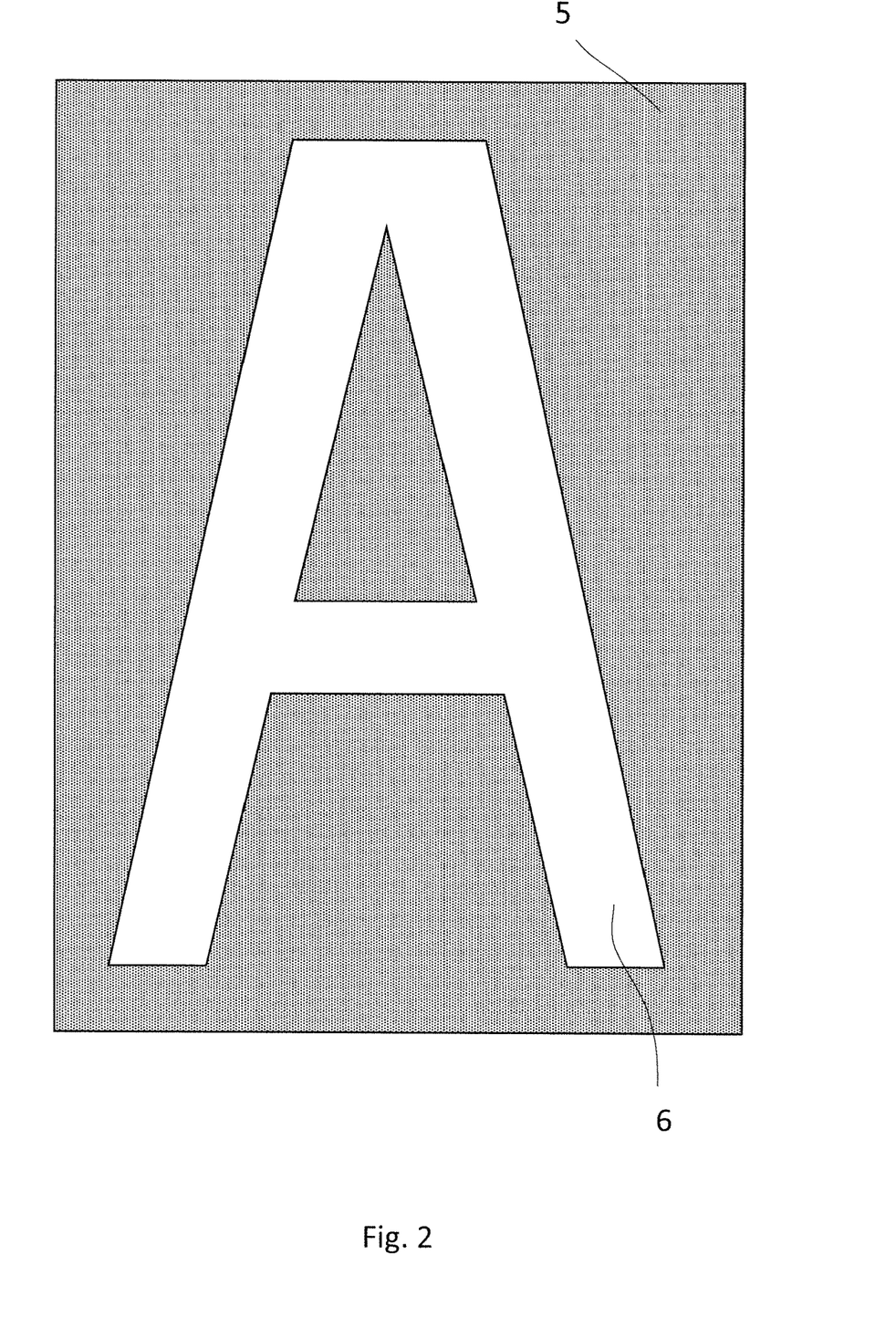
FIG. 2 schematically shows a detailed view of the pattern of interest of FIG. 1 being an illuminated region of the modified retinal area.

FIG. 2 schematically shows a detailed view of a pattern of interest 6 being an illuminated region of the modified retinal area 5.

Figure 3:
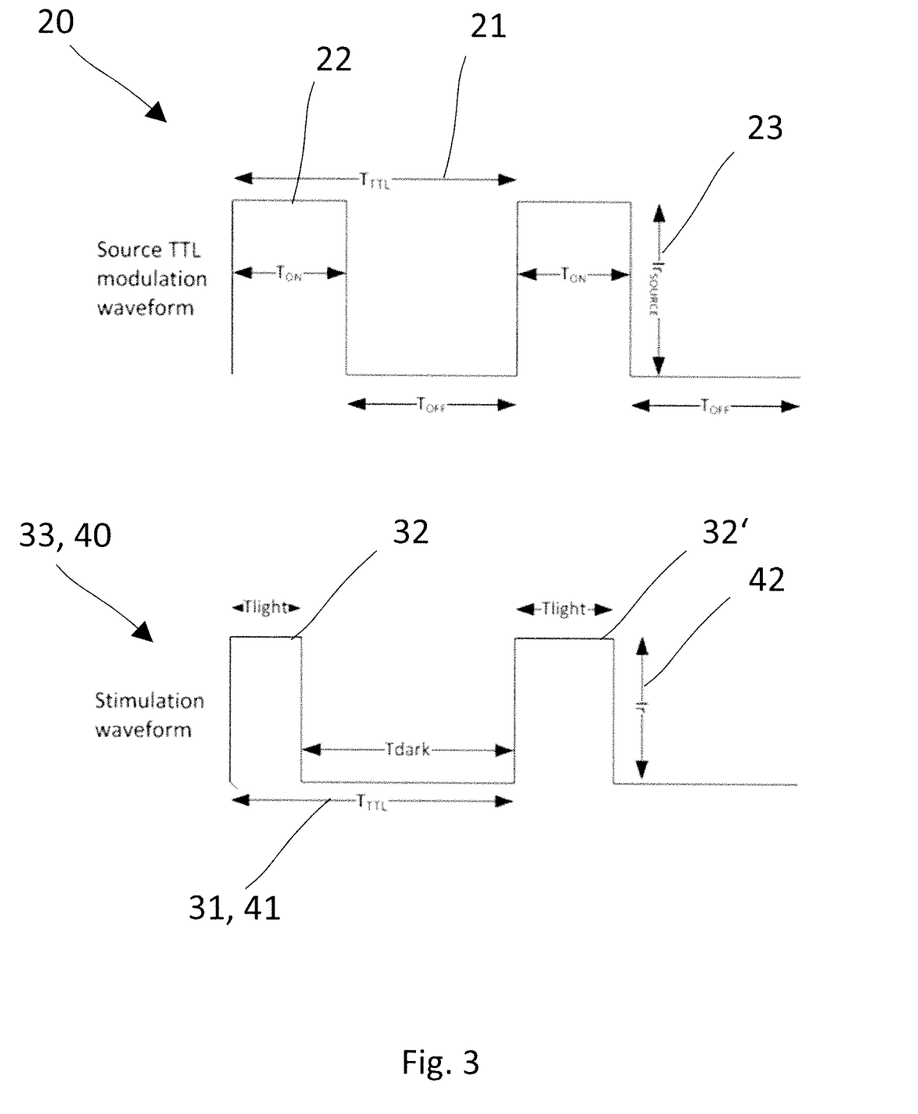
FIG. 3 schematically shows a pulsed input light beam comprising the shape of a pulsed wave and a corresponding modulated pulsed sub-beam.

The input light beam 20 is pulsed having a waveform comprising the shape of a pulsed wave, as can be taken for instance from FIG. 3. The light beam 20 is pulsed by means of the light source 2 in that it comprises a constant irradiation 23, which is irradiated during each duty cycle 22 in each period 21 of the wave of the light beam 20.

Accordingly, as the output beam 4 is essentially based on the input beam 20, also the output beam 4 is pulsed, wherein a period of the output beam 4 and also a duty cycle of the output beam 4 generally corresponds to the period 21 and the duty cycle 22 of the input light beam 20. Hence, the pattern of interest 6 comprises an even irradiation over its entire surface, as depicted in FIG. 2.

In order to achieve the ability to provide also grayscale information into the output beam 4, the device 1 is furthermore formed and adapted to perform a pulse width modulation individually for each of the sub-beams 40. The latter is achieved by individually controlling a modulation duty cycle 32 of each of the individual micromirrors 30.

With other words, the time each of the micromirrors 30 is oriented in a position such that it reflects the input light beam 20 and thereby providing a sub-beam 40 contributing to the output beam 4 may be individually set different for each micromirror 30 depending on the corresponding grayscale level of the pixel in the pattern of interest 6 correlated to the respective micromirror 30.

In this regard, the pulse width modulation is performed, such that for each micromirror pulsing cycle, the modulation duty cycle 32 may individually adjusted. That is, when a camera keeps constantly capturing images, a change in the brightness level of a pixel may lead to a change of the modulation duty cycle 32. Hence, when the brightness level increases, also the modulation duty cycle 32 is correspondingly increased, or vice versa.

Preferably, as shown in FIG. 3, a modulation period 31 of the micromirror pulsing 33, which corresponds to an output beam period 41, is synchronized with the period 21 of the input light beam 20. Moreover, optionally, a maximum possible modulation duty cycle 32 of the micromirrors 30 is set to correspond to the constant duty cycle 22 of the input light beam 20.

Thereby, it may be achieved that no operation of micromirrors 30 is performed, when the light source 2 does not provide irradiance. This may hence safe operation power of the device 1.

In FIG. 3, two subsequence micromirror pulsing cycles for an individual micromirror 30, and hence for a sub-beam 40 are shown. The first shown modulation duty cycle 32 is smaller than the second shown modulation duty cycle 32', wherein the irradiance 42 is constant for each modulation duty cycle 32, 32'. Hence, a patient comprising the retinal implant will perceive the respective zone of the image to become brighter.

As can be furthermore seen in this figure, both modulation duty cycles 32, 32' are shorter than the duty cycle 22. Hence, the patient perceives a brightness level lower than a maximum possible perceivable brightness. For safety reasons, the duty circle 22 is limited to 30% of the period 21, thereby preventing damages at the retina due to an excessive irradiation.

In order to provide a redundant safety system, also the duty cycle 32 of the micromirrors 30 is limited to be 30% of the period 21 or the modulation period 31, respectively. Hence, in case the light source erroneously emits a constant light beam, the maximum possible duty cycle of the output beam 4 is limited to the duty cycle 32 of the micromirrors 30.

Hence, even if the safety setting for the light source 2 fails, it can be achieved that no excessive irradiance hits the retina. Moreover, also if the micromirrors 30 fail to pulse and/or are stuck in an "ON" position, the source pulsing forbids to have a pulse duration of the output light beam 4 higher than the source pulse duration, that is than duty circle 22.

Figure 4:
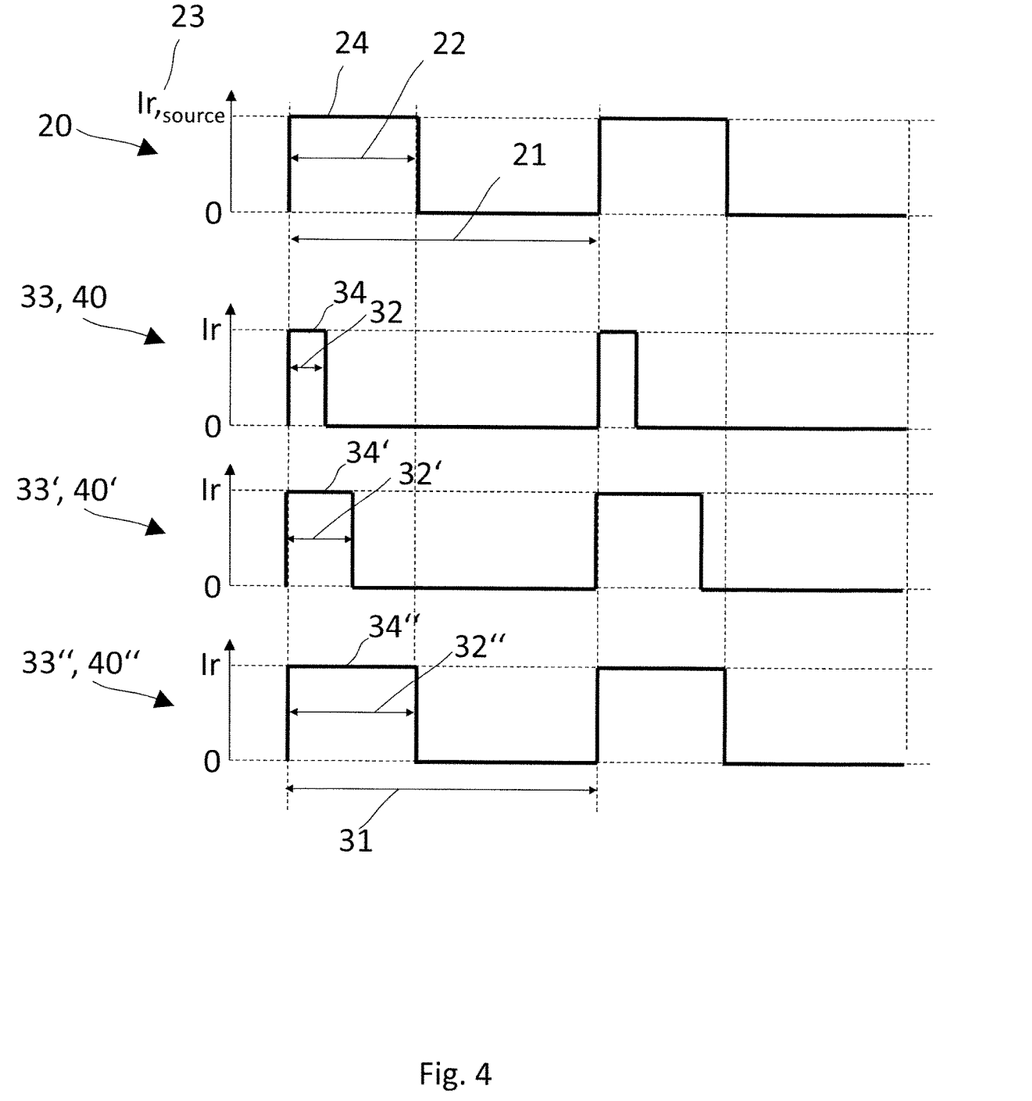
FIG. 4 schematically shows another input light beam having substantially the form of a pulse wave and corresponding micromirror pulsing for three different micromirrors, resulting in three different sub-beams.

FIG. 4 shows an exemplary embodiment of a waveform of an input light beam 20 having substantially the form of a pulse wave comprising a constant source irradiance 23, a constant duty cycle 22 of the pulse 24, and a constant period 21.

Below the wave form of the input light beam 20, micromirror pulsing 33, 33', 33" for three different micromirrors 30 is shown, resulting in three different sub-beams 40, 40', 40".

The micromirror pulsing 33, 33', 33" distinguish from each other in that their duty cycles 32, 32', 32" of the corresponding pulses 34, 34', 34" differ.

That is, the radiant power of each of the sub-beams 40, 40', 40" distinguished from the others, wherein the first sub-beam 40 comprises a lower radiant power than the second and the third sub-beams 40', 40", and the second sub-beam 40' comprises a lower radiant power than the third sub-beam 40".

Consequently, when for instance a first zone 61 of the pattern of interest 6 is irradiated with sub-beams corresponding to sub-beam 40, a patient comprising the retinal implant perceives a darker greyscale value than in a second zone 62 irradiated with sub-beams corresponding to sub-beam 40', and a third zone 63 irradiated with sub-beams corresponding to sub-beam 40", wherein the latter comprises the brightest grayscale value.

Figure 5:
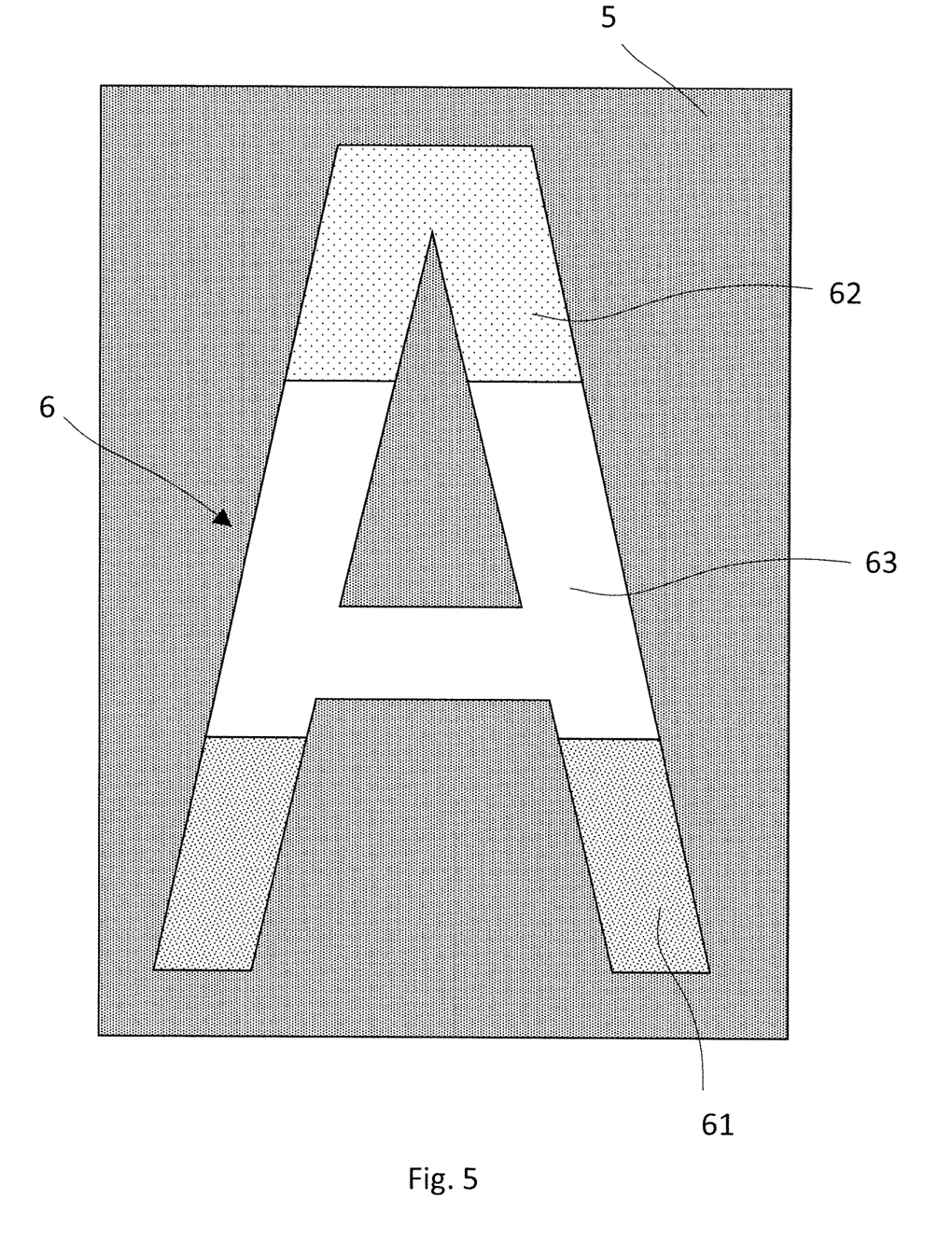
FIG. 5 shows schematically an example for zones of the pattern of interest projected at a retinal implant via the sub-beams of FIG. 5.

An example for the above-mentioned zones 61, 62, 63 of the pattern of interest 6 projected at a modified retinal area 5 comprising retinal implant can be taken from FIG. 5.

Hence, by the above described device 1 and a corresponding method, it is possible to provide a patient comprising a photosensitive retinal implant with patterns that have different grey levels.

Moreover, by the aforementioned, power consumption for performing the method and/or for operation of the device 1 can be reduced and/or optimized, since the light source can be switched off between pulses and therefore consume less energy between pulses and thus reduce power consumption.

It will be obvious for a person skilled in the art that these embodiments and items only depict examples of a plurality of possibilities. Hence, the embodiments shown here should not be understood to form a limitation of these features and configurations. Any possible combination and configuration of the described features can be chosen according to the scope of the invention.

| List of reference numerals | |
| --- | --- |
| 1 | Device |
| 2 | light source |
| 20 | input light beam |
| 21 | period |
| 22 | duty cycle |
| 23 | irradiance |
| 24 | pulse |
| 3 | micromirror array |
| 30 | micromirror |
| 31 | modulation period |
| 32 | modulation duty cycle |
| 33 | micromirror pulsing |
| 34 | pulse |
| 4 | output beam |
| 40 | sub-beam |
| 41 | output beam period |
| 42 | irradiance |
| 5 | modified retinal area 6 pattern of interest |
| 61 | first zone |
| 62 | second zone |
| 63 | third zone |

The invention claimed is:

1. A method for projecting a pattern of interest on a modified retinal area of a human eye, comprising:
   providing a pulsed input light beam,
   modulating and dividing the pulsed input light beam into a pulsed and modulated light pattern of modulated pulsed sub-beams based on a pattern of interest, wherein the modulated light pattern forms a pulsed output beam reflecting the pattern of interest,
   characterized by
   performing an individual pulse width modulation of a modulation duty cycle of the modulated individual sub-beams forming the output beam,
   wherein a modulation period is synchronized with the period of the pulsed input light beam.

2. The method according to claim 1, wherein the input light beam comprises a constant peak irradiance.

3. The method according to claim 1, wherein a maximum individual modulation duty cycle of the individual sub-beams corresponds to the duty cycle of the pulsed input light beam.

4. The method according to claim 1, wherein the duty cycle of the pulsed input light beam is equal to or smaller than 0.5 to the period of the pulsed input light beam.

5. The method according to claim 1, wherein the pattern of interest is obtained by capturing visual information, preferably an image, and dividing the captured visual information into a pattern of pixels forming the pattern of interest, wherein the pixels at least reflect different brightness values if present within the visual information.

6. The method according to claim 1, wherein the input light beam comprises substantially the form of a pulse wave.

7. The method according to claim 1, wherein the input light beam comprises a constant period.

8. The method according to claim 1, wherein the input light beam comprises a constant duty cycle.

9. The method according to claim 1, wherein the input light beam comprises a duty cycle of the input light beam that is controlled.

10. The method according to claim 1, wherein a maximum possible modulation duty cycle of the sub-beams is equal to or smaller than 0.5 to the period of the pulsed input light beam.

11. A device for projecting a pattern of interest on a modified retinal area of a human eye, comprising:
a light source for providing a pulsed input light beam,
a modulation micromirror array for modulating and dividing the pulsed input light beam into a modulated light pattern of modulated pulsed sub-beams, wherein an orientation of each of the micromirrors of the micromirror array is individually controllable based on a pattern of interest, such that the sub-beams form a pulsed output beam reflecting the pattern of interest, characterized in that
the device is formed and adapted to perform an individual pulse width modulation of the sub-beams forming the output beam by individually controlling a modulation duty cycle of the individual micromirrors, and
a modulation period of the orientation control of the micromirrors is synchronized with the period of the pulsed input light beam.

12. The device according to claim 11, wherein a maximum individual modulation duty cycle of the micromirrors corresponds to the duty cycle of the pulsed input light beam.

13. The device according to claim 11, wherein the duty cycle of the pulsed input light beam is equal to or smaller than 0.5 to the period of the pulsed input light beam.

14. The device according to claim 11, further comprising a camera for capturing visual information.

15. The device according to claim 11, further comprising a processing unit for dividing a captured visual information into a pattern of pixels forming the pattern of interest, wherein the pixels at least reflect different brightness values if present within the visual information.

16. The device according to claim 11, wherein a maximum possible modulation duty cycle of the sub-beams is equal to or smaller than 0.5 to the period of the pulsed input light beam.

17. A method for projecting a pattern of interest on a modified retinal area of a human eye, comprising:
providing a pulsed input light beam,
modulating and dividing the pulsed input light beam into a pulsed and modulated light pattern of modulated pulsed sub-beams based on a pattern of interest, wherein the modulated light pattern forms a pulsed output beam reflecting the pattern of interest,
characterized by
performing an individual pulse width modulation of a modulation duty cycle of the modulated individual sub-beams forming the output beam,
wherein a maximum individual modulation duty cycle of the individual sub-beams corresponds to the duty cycle of the pulsed input light beam.

18. A method for projecting a pattern of interest on a modified retinal area of a human eye, comprising:
providing a pulsed input light beam,
modulating and dividing the pulsed input light beam into a pulsed and modulated light pattern of modulated pulsed sub-beams based on a pattern of interest, wherein the modulated light pattern forms a pulsed output beam reflecting the pattern of interest,
characterized by
performing an individual pulse width modulation of a modulation duty cycle of the modulated individual sub-beams forming the output beam,
wherein the pattern of interest is obtained by capturing visual information, preferably an image, and dividing the captured visual information into a pattern of pixels forming the pattern of interest, wherein the pixels at least reflect different brightness values if present within the visual information.

19. A device for projecting a pattern of interest on a modified retinal area of a human eye, comprising:
a light source for providing a pulsed input light beam,
a modulation micromirror array for modulating and dividing the pulsed input light beam into a modulated light pattern of modulated pulsed sub-beams, wherein an orientation of each of the micromirrors of the micromirror array is individually controllable based on a pattern of interest, such that the sub-beams form a pulsed output beam reflecting the pattern of interest, and
a camera for capturing visual information and a processing unit for dividing the captured visual information into a pattern of pixels forming the pattern of interest, wherein the pixels at least reflect different brightness values if present within the visual information
characterized in that
the device is formed and adapted to perform an individual pulse width modulation of the sub-beams forming the output beam by individually controlling a modulation duty cycle of the individual micromirrors.

\* \* \* \* \*